United States Patent [19]

Schlecht et al.

[11] 4,022,815

[45] May 10, 1977

[54] MANUFACTURE OF SUBSTITUTED GLYCINONITRILES

[75] Inventors: Helmut Schlecht, Ludwigshafen; Harry Distler, Bobenheim; Erwin Hartert, Ludwigshafen, all of Germany

[73] Assignee: BASF Aktiengesellschaft, Ludwigshafen (Rhine), Germany

[22] Filed: Jan. 16, 1976

[21] Appl. No.: 649,582

[30] Foreign Application Priority Data

Jan. 29, 1975 Germany .......................... 2503582

[52] U.S. Cl. ..................... 260/465.5 A; 260/534 R
[51] Int. Cl.² ........................................ C07C 121/44
[58] Field of Search ............................ 260/465.5 A

[56] References Cited

UNITED STATES PATENTS

| 2,860,164 | 11/1958 | Kroll et al. | 260/465.5 R |
| 3,409,666 | 11/1968 | Foreman | 260/465.5 A |
| 3,499,920 | 3/1970 | Daniels | 260/465.5 A |

Primary Examiner—Joseph P. Brust
Attorney, Agent, or Firm—Johnston, Keil, Thompson & Shurtleff

[57] ABSTRACT

N-Alkylglycinonitriles are manufactured by reaction of N-alkylamines with formaldehyde and hydrocyanic acid under specific conditions of temperature, reaction time and hydrocyanic acid concentration.

8 Claims, No Drawings

MANUFACTURE OF SUBSTITUTED GLYCINONITRILES

The N-alkylglycinonitriles obtainable by the process of the invention are valuable starting materials for the manufacture of dyes, fungicides, bactericides, textile assistants, and assistants used in dental cosmetics, gas purification and water repellent finishing.

The present invention relates to a process for the manufacture of substituted glycinonitriles by reaction of amines with formaldehyde and hydrocyanic acid under specific conditions of temperature, reaction time and hydrocyanic acid concentration.

German Patent No. 656,350 discloses that glycollic acid nitrile can be reacted with excess methylamine in aqueous solution under pressure, to give sarcosinonitrile. This patent recommends using an excess of up to 10 moles of methylamine per mole of hydroxyacetonitrile if good yields of sarcosinonitrile are to be achieved. If stoichiometric amounts are used, substantial amounts of the nitrile of methyldiglycollamic acid, which is difficult to remove, are produced.

Another method of preparation of N-alkyl-substituted glycinonitriles starts from formaldehyde in the presence of sodium bisulfite compounds, the aldehyde being reacted with sodium cyanide and aliphatic amines. The use of sodium cyanide and sodium bisulfite presents environmental problems if carried out industrially, due to the formation of by-products consisting of alkali metal salts which may contain residual cyanides. The use of the amines, in this reaction, in the form of salts, eg. chlorides, has also been disclosed (Jean Mathieu and Jean Weil-Raynal, Formation of C-C-bonds, vol. I, pages 442-446 (Georg Thieme Verlag Stuttgart 1973).

All these processes are unsatisfactory in that they fail to provide a simple and economical method, a good yield of end product and an easy method of working up, particularly in respect of protection of the environment and purification of waste water.

It is an object of the present invention to provide a new process for the simpler and more economical manufacture of N-alkylglycinonitriles in better yield and better purity.

We have found that this object is achieved and that substituted glycinonitriles of the formula

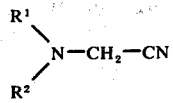

where R¹ and R² are identical or different and each is an aliphatic radical, and R² may also be hydrogen, are obtained in an advantageous manner by reaction of formaldehyde with amines and cyano compounds when N-alkylamines of the formula

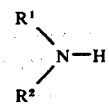

where R¹ and R² have the above meaning, are reacted with formaldehyde and hydrocyanic acid in the presence of water for from 0.1 to 4 hours at from 0° to 40° C, the concentration of hydrocyanic acid during the reaction being not more than 0.1% by weight, based on the reaction mixture.

If dimethylamine is used, the reaction can be represented by the following equation:

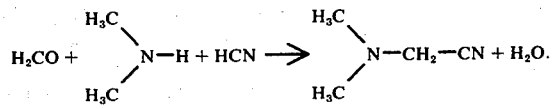

Compared with conventional processes, the process of the invention is able to give certain substituted glycinonitriles more simply and more economically and in better yield and purity. The process is particularly suitable for industrial-scale working and for continuous operation, presents no major problems of pollution of effluent and is less detrimental to the environment. Byproducts, eg. nitriles of alkyldiglycollamic acids or methylolamines resulting from the presence of formaldehyde are not formed to a signficant degree. All these advantageous aspects are surprising in view of the prior art.

The formaldehyde may be used as liquid or as gas, in general in the form of an aqueous solution which is suitably of from 10 to 50 percent strength by weight and preferably of from 30 to 40 percent strength by weight. The hydrocyanic acid may be used as gas or, advantageously, as a liquid. The starting amine II may be used as such or, advantageously, in solution, preferably in aqueous solution; suitable solutions are of from 40 to 60 percent strength by weight. The three starting materials may be reacted in stoichiometric amounts, or each of the components may be employed in excess, preferably in an amount of from 0.1 to 2 moles of amine and/or from 0.01 to 0.1 mole of hydrocyanic acid per mole of formaldehyde (taken as 100% strength). Preferred starting materials II and accordingly preferred end products I are those where R¹ and R² may be identical or different and each is alkyl of 1 to 8, especially of 1 to 4, carbon atoms, and R² may also be hydrogen. The above radicals may be substituted by groups which are inert under the reaction conditions, eg. alkyl and alkoxy each of 1 to 4 carbon atoms.

Examples of suitable starting materials II are methylamine, ethylamine, n-propylamine, isopropylamine, n-butylamine, isobutylamine, sec.-butylamine, tert.-butylamine, pentylamine, pentyl-2-amine, pentyl-3-amine, n-hexylamine, n-heptylamine, n-octylamine, n-nonylamine, n-decylamine, 2-ethylhexylamine, 2,2,6-trimethyl-n-pentylamine, 2-ethylpentylamine, 3-ethylpentylamine, 2,3-dimethyl-n-butylamine, 2,2-dimethyl-n-butylamine, 2-methylpentylamine, 3-methylpentylamine, 2,2,4-trimethylpentylamine, 2-methylheptylamine, 3-methylheptylamine, 4-methylheptylamine, 3-ethylhexylamine, 2,2-dimethylhexylamine, 2,3-dimethylhexylamine, 2,4-dimethylhexylamine, 2,5-dimethylhexylamine, 3,3-dimethylhexylamine, 3,4-dimethylhexylamine, 2-methyl-3-ethylpentylamine, 3-methyl-3-ethylpentylamine, 2,2,3-trimethylpentylamine, 2,2,4-trimethylpentylamine, 2,3,3-trimethylpentylamine, 2,3,4-trimethylpentylamine and 2,2,3,3-tetramethylbutylamine; di-(methyl)-amine, di-(ethyl)-amine, di-(n-propyl)-amine, di-(isopropyl)-amine, di-(n-butyl)-amine, di-(isobutyl)-amine, di-(sec.-butyl)-amine, di-(tert.-butyl)-amine, di-(pentyl)-amine, di-(pentyl-2)-amine, di-(pentyl-3)-amine, di-(n-hexyl)-amine, di-(n-heptyl)-amine, di-(n-octyl)-amine, di-(n-nonyl)-amine, di-(n-decyl)-amine, di-(2-ethylhexyl)- amine, di-(2,2,6-trimethyl-n-pentyl)-amine, di-(2-ethylpentyl)-amine, di-(3-ethylpentyl)-amine, di-(2,3-dimethyl-n-butyl)-amine, di-(2,2-dimethyl-n-butyl)-amine, di-(2-methylpentyl)-amine, di-(3-methylpentyl)-amine, di-(2,2,4-trimethylpentyl)-amine, di-(2-methylheptyl)-amine, di-(3-methylheptyl)-amine, di-(4-methyl-heptyl)-amine, di-(3-ethylhexyl)-amine, di-(2,2-dimethylhexyl)-amine, di-(2,3-dimethylhexyl)-amine, di-(2,4-dimethylhexyl)-amine, di-(2,5-dimethylhexyl)-amine, di-(3,3-dimethylhexyl)-amine, di-(3,4-dimethylhexyl)-amine, di-(2-methyl-3-ethyl-pentyl)-amine, di-(3-methyl-3-ethylpentyl)-amine, di-(2,2,3-trimethylpentyl)-amine, di-(2,2,4-trimethylpentyl)-amine, di-(2,3,3-trimethylpentyl)-amine, di-(2,3,4-trimethylpentyl)-amine and di-(2,2,3,3-tetramethylbutyl)-amine; and corresponding amines having 2 of the above radicals which, however, are different from one another, eg. methylethylamine.

The reaction is carried out at from 0° to 40° C, preferably from 15° to 25° C, under reduced pressure or superatmospheric pressure or preferably under atmospheric pressure, batchwise or, preferably, continuously. Water is used, preferably in the form of an aqueous formaldehyde solution and/or aqueous amine solution, and in addition water is also formed during the reaction; advantageously a total amount of from 1 to 6, preferably from 3 to 4, moles of water, per mole of formaldehyde, is used. Hydrocyanic acid is added before and during the reaction in such an amount that the concentration during the reaction is not more than 0.1% by weight, preferably from 0.01 to 0.1% by weight, and especially from 0.05 to 0.1% by weight, of hydrocyanic acid, based on the reaction mixture. The reaction time (or, in continuous operation, the residence time) is from 0.1 to 4, and preferably from 1 to 2, hours. Preferably, water is the sole solvent, but, if appropriate, organic solvents which are inert under the reaction conditions may also be used. Examples of suitable solvents are aromatic hydrocarbons, eg. toluene, benzene, ethylbenzene, o-, m- and p-xylene, isopropylbenzene or methylnaphthalene; aliphatic or cycloaliphatic hydrocabons, eg. heptane, α-pinene, pinane, nonane, o-, m- and p-cymene, gasoline fractions of boiling range from 70° to 190° C, cyclohexane, methylcyclohexane, petroleum ether, decalin, hexane, ligroin, 2,2,4-trimethylpentane, 2,2,3-trimethylpentane, 2,3,3-trimethylpentane and octane, as well as mixtures thereof. Suitable amounts of solvent to use are from 40 to 10,000% by weight, preferably from 50 to 1,500% by weight, based on starting material II.

The reaction may be carried out as follows: a mixture of formaldehyde, water, hydrocyanic acid and starting amine II, if appropriate together with an organic solvent, is kept at the reaction temperature for the length of the reaction time. Hydrocyanic acid is added to the starting mixture and is also added, in portions or continuously, during the reaction so that the hydrocyanic acid concentration mentioned above is maintained during the entire reaction time. A silver-calomel electrode is conveniently used for continuous measurement of the hydrocyanic acid concentration. Finally, the end product may be isolated from the reaction mixture by conventional methods, eg. by distillation or extraction with, eg., cyclohexane, followed by distillation of the solvent.

In a preferred embodiment, the product is directly used for saponification, without first isolating it from the reaction mixture. The saponification of the product I may be carried out by conventional methods, as a rule in an alkaline medium, preferably in aqueous solutions of alkaline earth metal hydroxides or alkali metal salts such as sodium carbonate, bicarbonate, acetate or formate or potassium carbonate, bicarbonate, acetate or formate. Sodium hydroxide solution and potassium hydroxide solution are preferred. For example, mixtures containing from 30 to 40 percent by weight of the end product in such solutions are used and the saponification is suitably carried out at a pH of from 9 to 14 and at from 0° to 150° C, especially from 45° to 115° C, for from 2 to 30 hours. For example, the alkali, alkali metal salts or aqueous solutions of these compounds are added to the mixture and the product I is saponified in the mixture, under the above conditions. It is advantageous to carry out the saponification with from 1 to 2 equivalents of alkali or alkali metal salt, based on isolated product I, or with from 1 to 6 equivalents of alkali or alkali metal salt, based on the non-isolated product I present in the reaction mixture as described above. In an advantageous embodiment, the reaction mixture passes through several, preferably 2 or 3, different saponification stages at progressively increasing temperature, eg. through the kettles of a stirred kettle cascade. If a two-stage saponification is used, the first stage (first stirred kettle) preferably uses temperatures of from 55° to 110° C. and a residence time of from 3 to 20 hours and the second stage (second stirred kettle) preferably uses temperatures of from 45° to 70° C and a residence time of from 3 to 10 hours; in three-stage saponification, the preferred conditions are temperatures of from 55° to 60° C and a residence time of from 2 to 3 hours in the first stage, temperatures of from 90° to 95° C and a residence time of from 6 to 8 hours in the second stage and temperatures of from 110° to 115° C and a residence time of from 6 to 8 hours in the third stage. By using this stepwise saponification, discolorations and losses in yield can, surprisingly, be avoided. The salt of the substituted glycine corresponding to the product I may then be isolated from the saponification mixture by conventional methods, eg. by evaporation.

The substituted glycinonitriles obtainable by the process of the invention are valuable starting materials for the manufacture of dyes, fungicides, bactericides, textile assistants, and assistants in the fields of dental cosmetics, gas purification and water-proofing. Regarding their use, reference may be made to the publications cited above and to Ullmanns Encyklopadie der technischen Chemie, volume 8, pages 212–213.

In the Examples which follow, parts are by weight.

EXAMPLE 1 a. Per hour, 196 parts of a 30 percent strength by weight aqueous formaldehyde solution, 54 parts of liquid hydrocyanic acid and 214 parts of a 42 percent strength by weight dimethylamine solution are slowly introduced into a stirred kettle at 18° C, under conditions such that during the reaction the hydrocyanic acid concentration does not exceed 0.1% by weight, based on the total mixture. The average hydrocyanic acid concentration is from 0.08 to 0.09% by weight. The reaction mixture is then distilled. Per hour, 330 parts (98% of theory) of N-dimethylglycinonitrile of boiling boint 63 C at 41 mm Hg, and of $n_D^{20} = 1.4107$, are obtained.

b. The reaction is carried out analogously to Example (1a), but the product I is not isolated and is instead processed directly. After a residence time of 2 hours, 464 parts per hour of the reaction mixture are run into the saponification kettle, to which 378 parts of 30 percent strength by weight potassium hydroxide solution are added per hour at from 50° to 55° C. After a residence time of 2½ hours the saponification solution is heated to from 90° to 95° C in the first kettle, equipped with a condenser and off-gas outlet, of a cascade. After a residence time of 8 hours, the saponification solution is transferred to a second saponification kettle, equipped with a condenser, where a temperature of from 110° to 115° C is maintained. At the same time, 200 parts of water and 550 parts of steam (at 170° C) are introduced per hour. 34 parts of gaseous ammonia and 1,000 parts of a 3 percent strength by weight ammonia solution are discharged per hour through a heated column surmounted by a reflux condenser. Per hour, 558 parts of a 42 percent strength by weight aqueous colorless solution of the potassium salt of dimethylglycine are obtained.

EXAMPLE 2 a. Analogously to Example 1, 400 parts of 30 percent strength by weight formaldehyde 108 parts of liquid hydrocyanic acid and 458 parts of 40 percent strength by weight methylamine solution are introduced hourly at 18° C into a stirred kettle, without exceeding a hydrocyanic acid concentration of 0.1% by weight in the reaction mixture. After a mean residence time of 30 minutes, the reaction mixture is transferred to a reactor which is at a temperature of 20° C. Here the cyanide concentration falls to less than 500 ppm, based on total mixture. The average hydrocyanic acid concentration is 0.04% by weight. Per hour, 996 parts of the reaction mixture are obtained, and are dehydrated azeotropically with toluene to give 270 parts per hour (96.4% of theory) of N-methylglycinonitrile of boiling point 65° C at 20 mm Hg.

b. The reaction is carried out analogously to Example (2a) but the end product I is not isolated and instead is processed directly. After a mean residence time of one hour, 966 parts per hour of reaction mixture are run, analogously to Example 1, into a saponification kettle, into which 200 parts of water and 548 parts of a 30 percent strength by weight sodium hydroxide solution are introduced per hour at 45° C. After a residence time of 2½ hours, the saponification solution is transferred to another saponification kettle, which is at 100° C. After a mean residence time of 4 hours, the mixture is run into a post-reactor, where the reaction is completed in the course of a residence time of 3 hours at 110° C. 1,034 parts per hour of a 38 percent strength by weight sodium sarcosinate solution of density 1.2 are obtained, whilst at the same time ammonia, methylamine and water are evaporated off.

We claim:
1. A process for the manufacture of an N-alkylglycinonitrile of the formula

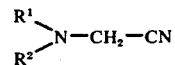   I, wherein $R^1$ and $R^2$ are identical or different and each is alkyl of 1 to 8 carbon atoms, $R^2$ may also be hydrogen, and each of $R^1$ and $R^2$ as alkyl may also be substituted by alkyl or alkoxy of 1 to 4 carbon atoms each, which comprises reacting an N-alkylamine of the formula

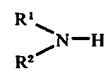   II, wherein $R^1$ and $R^2$ have the above meaning, with formaldehyde and hydrocyanic acid in the presence of water for from 0.1 to 4 hours at from 0° C. to 40° C., the concentration of hydrocyanic acid during the reaction being not more than 0.1% by weight, based on the reaction mixture.

2. A process as claimed in claim 1, wherein the reaction is carried out with from 0.1 to 2 moles of amine per mole of formaldehyde (taken as 100% strength).

3. A process as claimed in claim 1, wherein the reaction is carried out at from 15° to 25° C.

4. A process as claimed in claim 1, wherein the reaction is carried out with a total of from 1 to 6 moles of water per mole of formaldehyde.

5. A process as claimed in claim 1, wherein the reaction is carried out under conditions such that the concentration of hydrocyanic acid during the reaction is from 0.01 to 0.1% by weight, based on the reaction mixture.

6. A process as claimed in claim 1, wherein the reaction is carried out under conditions such that the concentration of hydrocyanic acid during the reaction is from 0.05 to 0.1% by weight, based on the reaction mixture.

7. A process as claimed in claim 1, wherein the reaction is carried out for from 1 to 2 hours.

8. A process as claimed in claim 1, wherein the reaction is carried out in the presence of from 40 to 10,000% by weight, based on starting material II, or an organic solvent which is inert under the reaction conditions.

* * * * *